US009545479B2

(12) United States Patent
Orr et al.

(10) Patent No.: US 9,545,479 B2
(45) Date of Patent: Jan. 17, 2017

(54) SYRINGE ASSIST DEVICE

(71) Applicants: Ronald Earl Orr, Belleville, MI (US); Ronda Waverly Orr, Westland, MI (US)

(72) Inventors: Ronald Earl Orr, Belleville, MI (US); Ronda Waverly Orr, Westland, MI (US)

(*) Notice: Subject to any disclaimer, the term of this patent is extended or adjusted under 35 U.S.C. 154(b) by 317 days.

(21) Appl. No.: 14/100,217

(22) Filed: Dec. 9, 2013

(65) Prior Publication Data
US 2014/0163479 A1 Jun. 12, 2014

Related U.S. Application Data

(60) Provisional application No. 61/734,758, filed on Dec. 7, 2012.

(51) Int. Cl.
*A61M 5/31* (2006.01)

(52) U.S. Cl.
CPC .... *A61M 5/3137* (2013.01); *A61M 2005/3139* (2013.01)

(58) Field of Classification Search
CPC ............. A61M 5/3135; A61M 5/3137; A61M 2005/3139
USPC .......................... 604/187, 195, 196, 227, 506
See application file for complete search history.

(56) References Cited

U.S. PATENT DOCUMENTS

| | | | | |
|---|---|---|---|---|
| 1,331,805 A | * | 2/1920 | Chance | A61M 5/31 604/227 |
| 4,068,661 A | * | 1/1978 | Hennings | A61M 5/3135 604/227 |
| 4,235,235 A | * | 11/1980 | Bekkering | A61M 5/3129 604/238 |
| 4,687,427 A | | 8/1987 | Seybold | |
| 4,687,472 A | * | 8/1987 | Gross | A61M 5/24 604/223 |
| 5,115,816 A | * | 5/1992 | Lee | A61M 5/1782 600/562 |
| 5,232,457 A | * | 8/1993 | Grim | A61M 5/24 604/195 |
| 5,554,133 A | | 9/1996 | Haffner et al. | |
| 5,573,514 A | | 11/1996 | Stiehl et al. | |
| 5,997,514 A | * | 12/1999 | Balestracci | A61M 5/3135 604/187 |
| 6,159,184 A | * | 12/2000 | Perez | A61M 5/3271 604/192 |

(Continued)

Primary Examiner — Nathan R Price
Assistant Examiner — Gerald Landry, II
(74) Attorney, Agent, or Firm — Carrier Blackman & Associates, P.C.; Joseph P. Carrier; Anne G. Sabourin

(57) ABSTRACT

A finger grip extension for a syringe is configured to increase the leverage the hand of an operator on the plunger of a syringe during injection of medical fluid into, or withdrawal of medical fluid from a body site. The finger grip extension for a syringe is used with a syringe having a barrel portion having an open proximal end and a distal end for mounting a medical fluid conduit thereon. The open proximal end of the syringe barrel terminates in a rim or flange. The syringe also includes a plunger having a proximal end and a distal end for insertion into the open proximal end of a syringe. The extension grip includes an upwardly extending portion located inside or outside of a syringe barrel. The upwardly extending portion includes a finger support at the uppermost portion thereof.

4 Claims, 1 Drawing Sheet

(56) References Cited

U.S. PATENT DOCUMENTS

| | | | | |
|---|---|---|---|---|
| 6,719,735 B1* | 4/2004 | Gammon | ............ | A61M 5/3148 |
| | | | | 604/218 |
| 7,118,556 B2* | 10/2006 | Nerney | ............... | A61M 5/3148 |
| | | | | 604/181 |
| 7,611,495 B1* | 11/2009 | Gianturco | ......... | A61M 5/31501 |
| | | | | 604/207 |
| 2002/0103461 A1* | 8/2002 | Asbaghi | ................ | A61M 5/326 |
| | | | | 604/198 |
| 2005/0215958 A1* | 9/2005 | Hawthorne | ........ | A61B 10/0283 |
| | | | | 604/227 |
| 2007/0106226 A1* | 5/2007 | Croll | .................. | A61M 5/31511 |
| | | | | 604/199 |
| 2007/0208310 A1* | 9/2007 | Stadick | ............... | A61M 5/3148 |
| | | | | 604/187 |
| 2009/0093787 A1* | 4/2009 | Barbour | .............. | A61M 5/3137 |
| | | | | 604/506 |
| 2009/0124982 A1* | 5/2009 | Jimenez | ................ | A61M 5/315 |
| | | | | 604/228 |
| 2009/0182284 A1* | 7/2009 | Morgan | .............. | A61M 5/3137 |
| | | | | 604/198 |
| 2009/0234297 A1* | 9/2009 | Jennings | ............. | A61M 5/2033 |
| | | | | 604/195 |
| 2009/0240210 A1* | 9/2009 | Walton | ................ | A61M 5/3234 |
| | | | | 604/196 |
| 2012/0041384 A1* | 2/2012 | Finke | ...................... | A61M 5/34 |
| | | | | 604/194 |
| 2013/0184678 A1* | 7/2013 | Dimashkieh | .......... | A61M 5/326 |
| | | | | 604/506 |

\* cited by examiner

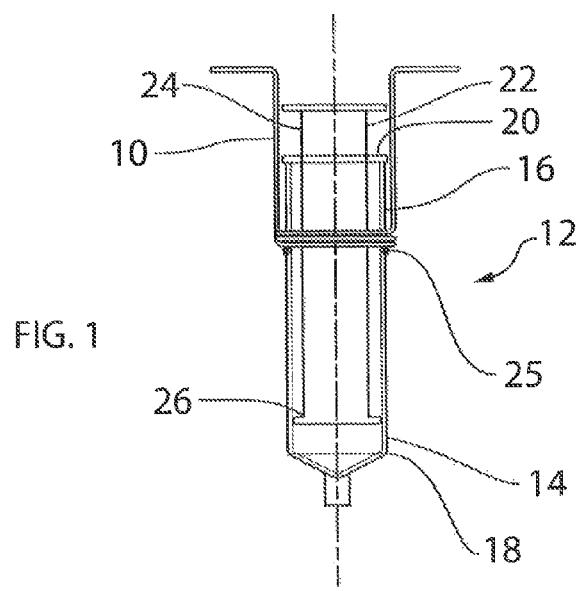
FIG. 1
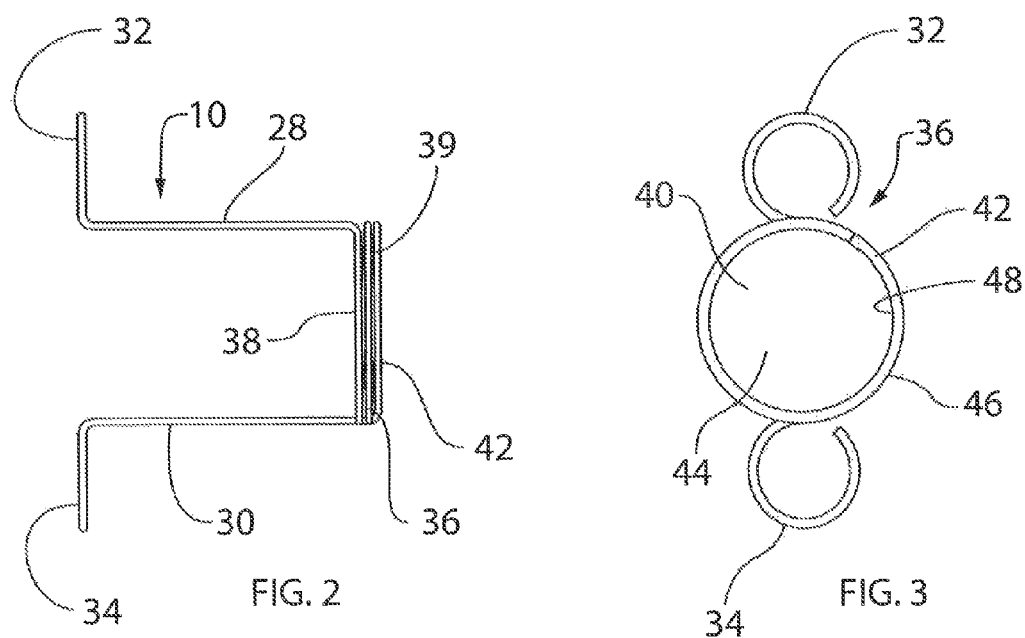
FIG. 2
FIG. 3

SYRINGE ASSIST DEVICE

CROSS-REFERENCE TO RELATED APPLICATIONS

This application claims priority to U.S. provisional application No. 61/734,758, filed Dec. 7, 2012. The entire subject matter of this priority document, including specification claims and drawings, is incorporated by reference herein.

BACKGROUND OF THE INVENTION

This invention relates generally to the field of syringes and, more particularly to an assist device for high-capacity hypodermic syringes. The assist device may be integral with the syringe or attached to a syringe. The device is used with or included in the design of syringes that are used to introduce fluids into bodily tissue. Such syringes may be used in introducing saline solutions, medications or other fluids into bodily tissue.

SUMMARY OF THE INVENTION

The present invention relates to a finger grip extension for a syringe, to increase the leverage of an operator on the plunger of a syringe during injection or withdrawal of medical fluid into or from a site. The finger grip extension for a syringe is used with a syringe having a barrel portion that has an open proximal end and a distal end for mounting a medical fluid conduit thereon. The open proximal end of the syringe barrel terminates in a rim or flange. The syringe also includes a plunger having a proximal end and a distal end for insertion into the open proximal end of a syringe. The extension grip includes an upwardly extending portion located inside or outside of a syringe, wherein said upwardly extending portion is of a length less than the length of the plunger, and extends to a point along the length of the fully or partially extended plunger. The grip may be adjustably positioned along the length of a syringe cartridge to adjust the length to the desired length. In one embodiment, the extension grip measures a length of between 0.25 and 0.75 of the length of the syringe plunger. In another embodiment, the extension grip measures a length of between 0.50 and 0.65 of the length of the syringe plunger. The upwardly extending portion further includes a finger support at the uppermost portion thereof. The finger support may be a collar around the circumference of the upwardly extending portion. Alternatively the finger support or supports may comprise a geometric surface integral with the upwardly extending portion, or may be an open ring shaped design, for insertion of the fingers. The grip may be integral with the syringe or removable from the syringe.

In one aspect of the invention the finger grip extension includes two upwardly extending arms or arm members which may be integral with a syringe or may be externally applied to the syringe. In the integral embodiment, the upwardly extending arm members may be formed when the syringe is molded. The arm members may be fixed or may be adjustable, and may be located internally or externally on the barrel of the syringe. The barrel may also include at least one positive lock member located on the inside or the outside of the barrel of the syringe to slidably receive and secure the grip. Multiple positive lock members may be placed at one or more locations along the barrel of the syringe. The lock members are integral with the syringe and comprise tabs that receive the grip.

In another aspect of the invention the grip has a U-shaped structure including two upwardly extending arm members integral with a cross member that has an upper surface and a lower surface. The cross member has an opening formed therein that corresponds to the shape of the syringe and allows the grip to be inserted over the barrel of the syringe. The grip may also include a seal having a circular opening formed therein, wherein the seal is attached to the lower surface of the cross member and the seal is of a shape and diameter substantially equal to the shape and diameter of the syringe barrel. The seal secures the grip to the outside of the barrel of the syringe when the grip is placed over the barrel of the syringe.

The invention is particularly useful in injecting large volumes of fluid into bodily tissues. The device provides leverage to better contact a plunger of a syringe in the instance where the syringe is large and/or where the user has small hands and the user's fingers do not extend the full length of the plunger at its extended position, with the thumb resting on the plunger.

For a more complete understanding of the present invention, the reader is referred to the following detailed description section. Throughout the following detailed description and in the drawings, like numbers refer to like parts.

BRIEF DESCRIPTION OF THE DRAWINGS

The foregoing summary, as well as the following detailed description of the preferred embodiments of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown. In the drawings:

FIG. 1 is a front view of a syringe.

FIG. 2 is a side view of one embodiment of the finger grip extension.

FIG. 3 is a top view of one embodiment of the finger grip extension.

DETAILED DESCRIPTION OF ILLUSTRATIVE EMBODIMENTS

Certain terminology is used in the following description for convenience only and is not limiting. The words "proximal," "distal," "upward," "bottom" and "top" designate directions in the drawings to which reference is made. The word "outwardly" refers to a direction away from the geometric center of the adapter or syringe, and designated parts thereof, in accordance with the present invention. Unless specifically set forth herein, the terms "a," "an" and "the" are not limited to one element, but instead should be read as meaning "at least one." The terminology includes the words noted above, derivatives thereof and words of similar import.

Referring to the drawings in detail, wherein like numerals indicate like elements throughout the several views, FIGS. 1-3 show a preferred embodiment of a syringe and an finger grip extension ("grip), generally designated 10 for a syringe, generally designated 12 and or in combination with the syringe 12. The grip 10 in one embodiment is a separate component or accessory from the syringe 12, such that the grip 10 can be easily installed onto at least a portion of the syringe 12 and/or is selectively removable therefrom. The grip 10 provides a user with an ergonomic advantage, as compared to the use of the syringe 12 without the adapter 10, while increasing the overall use of the syringe 12, particularly when the syringe is large and the user has smaller hands, or when a large volume of liquid, or highly viscous material is being administered. The grip may be used with any size syringe, but may be particularly useful in larger syringes administering 50 to 500 ml of fluid in an injection, and in one embodiment from 50 to 100 ml of fluid, and in another embodiment from 40 to 70 ml of fluid. The invention is useful for injecting any fluid into the body. In one instance the invention is used to inject saline into tissue during reconstruction procedures, such as, but not limited to, breast reconstruction. The invention is not intended to be limited to any particular size syringe adapter or in its use in any particular procedure.

As described in detail below, as shown in FIG. 1, the finger grip extension 10 (hereinafter, "grip") is adapted for a syringe 12 which includes a cylindrical barrel portion 14 having an inside diameter and an outside diameter and open proximal end 16 and a distal end 18, for mounting a medical fluid conduit thereon. The open proximal end 16 terminates in a rim or flange 20. The syringe also includes plunger 22, having an outside diameter equal to or slightly greater than the inside diameter of said cylindrical barrel, and slideably positioned in said cylindrical barrel after insertion into the open proximal end of a syringe 16. The plunger 22 has a proximal end 24 and a distal end 26, to facilitate use of a syringe during an injection or withdrawal of medical fluid into or from a site. The distal end of the plunger may include a plunger attached thereto (not shown), to improve the internal seal of the plunger with the inside of the syringe barrel. The syringe may also include one or more positive lock members 25, located on the barrel 14 of the syringe 12, to slidably receive the grip 10 at one or more locations along the barrel of the syringe in the embodiment of a grip that is slidable along the external barrel of the syringe. In one embodiment the positive lock members 25 may comprise tabs having an opening in the distal direction of the syringe barrel to receive and secure the grip 10, when the grip is engaged on the external barrel of the syringe.

Generally, the grip includes an upwardly extending portion located inside or outside of a syringe, wherein said upwardly extending portion is of a length less than the length of the syringe plunger, and extends to a point along the length of the fully or partially extended plunger to accommodate the hand size of the user. The extension grip provides an extension, above the flange of a syringe to support the fingers of the user, when a plunger is extended a distance further than the user can reach his or her fingers while having support fingers on the syringe flange and placing a thumb on the plunger. This allows the user to reach the extended plunger, when the distal end of the plunger is positioned at the proximal end of the syringe, or at any lesser extension of the plunger, that is beyond the reach of the user without the extension. In one embodiment, the extension grip measures a length of between 0.25 and 0.75 of the length of the syringe plunger. In another embodiment, the extension grip extends a length of between 0.40 and 0.65 of the length of the syringe plunger when the distal end of the plunger is positioned at the proximal end of the syringe. The upwardly extending portion of the grip further includes a finger support or supports, at the uppermost portion thereof. The finger support in one embodiment is a collar around the circumference of the upwardly extending portion. In another embodiment the finger support or support comprises two substantially horizontally extending tabs that are of any geometric configuration and extend substantially perpendicular to the plunger. The finger supports are integral with the upwardly extending portion. In another embodiment, the finger support comprises two open ring shaped planar surfaces for supporting the fingers. The finger support includes a proximal surface located facing the proximal end of the plunger and a distal surface facing the distal end of the plunger, and generally the fingers are placed on the distal surface of the finger rest for supporting the fingers when administering an injection.

In one embodiment, as shown in FIG. 2, the finger grip extension includes an upwardly extending portion comprising two arm members 28 and 30 respectively, for placement on either side of the outside of a syringe barrel (not shown), and each arm member includes a finger support 32 and 34 respectively, located at the top of the arm member, where said support extends horizontally outward from said arm member and is substantially perpendicular to the arm member. Alternatively the finger support can be an open ring shape to allow insertion of the fingers into the ring. In this embodiment the grip is removable from the syringe. The grip has a circumference equal to or slightly larger than the outside diameter of a syringe barrel and is removably or permanently secured to the outside of the syringe barrel.

FIG. 2 illustrates that the finger grip extension is a U-shaped structure having two upwardly extending arms 28 and 30, integral with a cross member 36, that has an upper surface 38 and a lower surface 39. As shown in FIG. 3, said cross member 36 has a circular opening 40 formed therein that allows the grip to be inserted over the barrel of the syringe. The grip also includes a seal 42 having a circular opening 44 formed therein, wherein the seal 42 is attached to the lower surface 39 of the cross member 36 and the seal 42 has an outside diameter 46 substantially equal to the diameter of the opening in the cross member and has an inner diameter 48 equal to or slightly smaller than the exterior syringe barrel, to provide a friction stop to secure the grip 10 to the external barrel of a syringe when the grip is placed over the barrel of a syringe. Suitable materials for the seal 42 include rubber or polymeric rubber components. The seal may be formed using an O-ring component of a flexible, gripping material such as a styrene-butadiene polymer, natural rubber or other flexible polymer.

FIG. 3 illustrates a top section of the U-shaped finger grip extension. The view illustrates the diameter of circular opening 40 formed in the cross member of the finger grip extension, as well as a configuration of the finger support 32 and 34 respectively, located at the top of the arms, where each support is an open ring shape extending perpendicular to the respective arm member on which it is located.

In an alternative embodiment, the cross member may be of any geometric shape, where the arms of the finger grip extension attach to either side of the cross member and the cross member includes a circular opening therein to allow the grip to be inserted over the barrel of the syringe.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

Although the present invention has been described herein with respect to a number of specific illustrative embodiments, the foregoing description is intended to illustrate, rather than to limit the invention. Those skilled in the art will realize that many modifications of the illustrative embodiment could be made which would be operable. All such modifications, which are within the scope of the claims, are intended to be within the scope and spirit of the present invention.

What is claimed is:

1. A removable finger grip extension for a syringe, provided to facilitate use of a syringe during an injection of medical fluid into an injection site, said syringe comprising a barrel portion having an open proximal end and a distal end, said open proximal end terminating in a rim, and a plunger for insertion into the open proximal end of said barrel portion, the plunger having a proximal end and a distal end, wherein said finger grip comprises a substantially u-shaped structure including a cross member with a circular opening formed therein for encircling an outer surface of a syringe barrel, a seal for securing the grip to the outer surface of the syringe barrel, and adjacent and perpendicular to the circular opening are two opposed arm portions for extending upwardly above the proximal end of the syringe, said arm portions configured to be located on opposite sides of a longitudinal central axis of a syringe barrel and to adjustably extend to a point along the length of the fully or partially extended plunger, and wherein said upwardly extending arm portions further include a finger support at an uppermost portion of each, and further comprising a plurality of positive lock members located on the outside of the barrel of the syringe, to slidably receive and secure the grip at selected locations along the barrel of the syringe.

2. A finger grip extension in combination with a syringe configured to facilitate the use of the syringe during an injection of medical fluid into an injection site, said combination comprising:

a) a cylindrical syringe barrel having an inside and an outside and
an open proximal end for receiving a plunger, said open proximal end terminating in a rim, said proximal end having a distal surface and a proximal surface; and a distal end for mounting a medical fluid conduit thereon;
b) a plunger being slideably disposed in said syringe barrel;
c) a removable finger grip extension comprising a substantially u-shaped structure including cross member with a circular opening formed therein for encircling an outer surface of a syringe barrel, and adjacent and perpendicular to the circular opening are two opposed arm portions, which extend upwardly above the proximal end of the syringe barrel, said arm portions being located on opposite sides of a longitudinal central axis of the syringe barrel, and said arm portions adjustably extend to a point along the length of a fully or partially extended plunger, and wherein said upwardly extending arm portions further include an integral finger support located at an uppermost portion of each; and
d) a plurality of positive lock members located on the outside of the barrel of the syringe, to slidably receive and secure the grip at selected locations along the outside of the barrel of the syringe.

3. The finger grip combination of claim 2, further comprising a seal having a circular opening formed therein, wherein the seal is attached to a lower surface of the cross member and the seal opening is of a diameter substantially equal to an outside diameter of the syringe barrel and the seal secures the grip to the barrel of the syringe when the grip is placed over the barrel of the syringe.

4. The finger grip combination of claim 2 wherein the syringe barrel fluid capacity is from 50 to 500 ml.

* * * * *